(12) United States Patent
Hudson et al.

(10) Patent No.: US 7,595,026 B2
(45) Date of Patent: Sep. 29, 2009

(54) SOLID PHASE EXTRACTION PIPETTE

(75) Inventors: William C. Hudson, Tustin, CA (US);
Wilford C. Downs, Dana Point, CA (US)

(73) Assignee: Varian, Inc., Palo Alto, CA (US)

( * ) Notice: Subject to any disclaimer, the term of this patent is extended or adjusted under 35 U.S.C. 154(b) by 555 days.

(21) Appl. No.: 10/554,648

(22) PCT Filed: May 28, 2004

(86) PCT No.: PCT/US2004/016904

§ 371 (c)(1),
(2), (4) Date: Oct. 26, 2005

(87) PCT Pub. No.: WO2004/106914

PCT Pub. Date: Dec. 9, 2004

(65) Prior Publication Data

US 2006/0216206 A1 Sep. 28, 2006

(51) Int. Cl.
*B01L 3/02* (2006.01)

(52) U.S. Cl. ........................... 422/100; 422/101

(58) Field of Classification Search ......... 422/100–102; 436/161; 210/198.2, 656; 29/419.1, 743
See application file for complete search history.

(56) References Cited

U.S. PATENT DOCUMENTS 6,200,474 B1  3/2001  Kopaciewicz et al.
6,210,570 B1*  4/2001  Holloway ............... 210/198.2

FOREIGN PATENT DOCUMENTS

EP  1 262 759 A1  12/2002
WO  WO 02/40131 A1  5/2002

OTHER PUBLICATIONS

Pedersen et al, "Dry Column Vacuum Chromatography," Synthesis, vol. 16, 2431-2434, 2001; pp. 1-7.*
Article by Hennion, Marie-Claire, entitled "Solid-Phase Extraction: Method Development, Sorbents, and Coupling with Liquid Chromatography", published by Journal of Chromatography A, Elsevier Science, NL, vol. 856, No. 1-2, Sep. 24, 1999, pp. 3-54.

* cited by examiner

*Primary Examiner*—Jill Warden
*Assistant Examiner*—Jameson Q Ma
(74) *Attorney, Agent, or Firm*—Cynthia R. Moore; Bella Fishman

(57) ABSTRACT

Solid phase extraction devices for sample preparation are disclosed, comprising a hollow conical tube having one narrower opening and one broader opening, wherein the narrower opening of the tube contains a solid phase extraction material comprising a functionalized monolithic sorbent, and wherein the solid phase extraction device is prepared by a combination of reduced pressure, positive pressure and mechanical compaction. The solid phase extraction devices are adapted for preparation of small sample volumes, and provide excellent recovery of analytes and good flow characteristics. Methods for preparing and using the solid phase extraction devices are disclosed.

7 Claims, 4 Drawing Sheets

Nor-fluoxetine, Quetiapine and Vardenafil at 50 ng/mL in Plasma Extracted Using Solid Phase Extraction Pipette and Analyzed Using HPLC

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial
<220> FEATURE:
<223> OTHER INFORMATION: chemically synthesized

<400> SEQUENCE: 1

Thr Phe Gln Ala Tyr Pro Leu Arg Glu Ala
1               5                   10

<210> SEQ ID NO 2
<211> LENGTH: 14
<212> TYPE: PRT
<213> ORGANISM: artificial
<220> FEATURE:
<223> OTHER INFORMATION: chemically synthesized

<400> SEQUENCE: 2

Arg Thr Lys Arg Ser Gly Ser Val Tyr Glu Pro Leu Lys Ile
1               5                   10

<210> SEQ ID NO 3
<211> LENGTH: 5
<212> TYPE: PRT
<213> ORGANISM: artificial
```

```
-continued

<220> FEATURE:
<223> OTHER INFORMATION: chemically synthesized

<400> SEQUENCE: 3

Leu Trp Met Arg Phe
1               5
```

SOLID PHASE EXTRACTION PIPETTE

FIELD OF THE INVENTION

This invention relates generally to devices for preparing samples for analysis, and in particular, for preparing small volume samples for analysis.

BACKGROUND OF THE INVENTION

Preparation of samples for analysis can consume a significant quantity of the sample, cause extraneous or spurious results in the analysis, and consume significant quantities of time, thus increasing the cost involved in the analysis. Sample preparation procedures generally involve removal of salts or other undesired components present in the sample, removal of undesired solvents or exchange of one solvent in which the intended analytes are dissolved for another solvent, concentration of analytes to a predetermined concentration, and the like. Thus, inadequate sample preparation procedures can result in loss of intended analytes as well as loss of time and increased costs, rendering analytical procedures costly, time consuming, unreliable, irreproducible and unsatisfactory. Numerous methods of preparing samples are available at present, including solid phase extraction ("SPE") to concentrate analytes from a liquid phase onto a solid phase, from which they can then be removed in relatively purer form for further analysis. Liquid phase extraction methods are also known, along with liquid-liquid phase extraction and liquid-liquid-liquid phase extraction methods.

Depending on the type of analysis to be performed, and detection method used, SPE can be tailored to remove specific interferences. Analysis of biological samples such as plasma and urine using high performance liquid chromatography (HPLC) or mass spectrometry generally requires SPE prior to analysis both to remove insoluble matter and soluble interferences, and also to pre-concentrate target compounds for enhanced detection sensitivity. Many biological samples contain salts or other ion suppressing components, which can be particularly troublesome when mass spectrometer based detection is used. SPE can also be used to perform a simple fractionation of a sample based on differences in hydrophobicity or functional groups of sample components, thereby reducing the complexity of the sample to be analyzed.

Devices designed for SPE typically include a chromatographic sorbent which allows the user to preferentially retain sample components. Once a sample is loaded onto the sorbent, a series of washing and elution fluids are passed through the device to separate contaminants or interfering compounds from intended sample analytes, and then to collect the target sample analytes for further analysis. SPE devices usually include a sample holding reservoir, a means for containing the sorbent, and a fluid conduit, or spout for directing the fluids exiting the device into suitable collection containers. The SPE device may be in a single well format, which is convenient and cost effective for preparing a small number of samples, or a multi-well format, which is well suited for preparing large numbers of samples in parallel. Multi-well formats are commonly used with robotic fluid dispensing systems. Typical multi-well formats include 48-, 96-, and 384-well standard plate formats. Fluids are usually forced through the SPE device and into the collection containers, either by drawing a vacuum across the device with a specially designed vacuum manifold, or by using centrifugal or gravitational force. Centrifugal force is generated by placing the SPE device, together with a suitable collection tray, into a centrifuge specifically designed for the intended purpose. However, all of these formats require relatively large amounts of sample and solvents, and require multiple fluid transfer steps.

Traditional SPE device designs have utilized packed beds of sorbent particles contained between porous filter discs that are contained within the SPE device. For example, U.S. Pat. No. 6,723,236 to Fisk describes SPE devices wherein sorbent particles are contained between two porous filter elements. The retention of compounds by the resulting packed beds is typically quite good, especially if the sorbent properties are carefully chosen. However, one drawback with conventional packed bed devices is that the void volume contained within the porous filters and packed bed requires that relatively large elution volumes be used to completely elute the target compounds. Typical elution volumes required to fully elute target compounds from a packed bed type SPE device fall in the range of 0.20-5 mL or more, depending on the size of the sorbent bed.

Thus, such devices are not suitable for small sample amounts or small volumes, and there is a need in the art for devices and methods for handling small sample sizes and quantities. To address these needs in the art, U.S. Pat. No. 5,906,796 to Blevins describes a solid phase extraction plate utilizing a plurality of solid phase extraction disks press fitted between the sidewalls of the chambers. A variety of extraction media were reported to be useful, in particular a nonpolar extraction medium containing silica bonded with hydrophobic groups available from Varian, Inc of Lake Forest, Calif., under the tradename SPEC®.

However, it would be convenient to incorporate solid phase extraction capabilities into microvolume liquid handling and dispensing devices themselves, thus eliminating steps in sample processing. Toward that end, U.S. Pat. No. 6,416,716 to Shukla describes a device for small sample preparation using tubes and columns such as capillaries or pipette tips in which particles of a separation medium are directly embedded in the solid material composing the device. Shukla further reports that the use of filters to hold separation media is problematic because filters slow the rate at which sample flows through the column and result in loss of sample on the filter material. Shukla states that loss of sample can be especially significant when very small sample volumes are involved. Shukla further states that filter-free columns that rely on a solid support matrix with embedded separation medium do exist, but that sample flow is low through these columns.

U.S. Pat. Nos. 6,048,457 and 6,200,474 to Kopaciewicz describe methods for preparing cast-in-place composite and/or nonfilled structures useful as sorptive or reactive media or for size based separations. The devices reportedly include a large amount of adsorptive particles entrapped in polymer while still maintaining the membrane three dimensional structure. In a preferred aspect, the methods are reported to be useful for preparing particles entrapped within a porous polymeric substrate in a pipette tip.

However, these devices and others suffer from limitations in methods of preparation that result in irreproducibility, poor flow rates, low capacity for adsorbing analytes, non-uniform flow rates, high manufacturing costs, and the like. Accordingly, there is a need in the art for improved SPE devices and methods for preparing them that overcome the limitations of the prior art devices.

SUMMARY OF THE INVENTION

Accordingly, it is a primary object of the invention to address the aforementioned need in the art by providing novel devices and methods that include a solid phase extraction capability in combination with liquid transfer capability.

It is another object of the invention to provide methods for preparing such solid phase extraction devices that exhibit reproducible performance and that do not result in the loss of valuable sample. It is a further object to provide methods for preparing solid phase extraction devices that provide greater and more precise analyte recovery from samples. It is yet another object to provide methods for preparing solid phase extraction devices that provide more reliable performance, both in terms of analyte recovery and ease of use.

Accordingly, solid phase extraction devices are provided for sample preparation, comprising a hollow conical tube having one narrower opening and one broader opening, wherein the narrower opening of the tube contains a solid phase extraction material comprising a functionalized monolithic sorbent, wherein the solid phase extraction device is prepared by a combination of reduced pressure, positive pressure and mechanical compaction. In a preferred embodiment, the solid phase extraction device is a pipette having a smaller opening and larger opening and a functionalized monolithic sorbent placed in the smaller opening (or tip) of the pipette. The functionalized monolithic sorbent is placed in the smaller opening of the pipette by a combination of reduced pressure, positive pressure and mechanical compaction.

The solid phase extraction material is a functionalized monolithic sorbent, comprising a glass fiber matrix embedded with a bonded phase comprising a metal oxide or metalloid oxide having reactive metal oxides capable of reacting with silanes, such as alkoxysilanes, aminosilanes, hydroxysilanes or halosilanes. Suitable metal oxides and metalloid oxides include silica, alumina, zeolite, mullite, zirconia, vanadia or titania, or mixtures or composites thereof. Likewise, the glass fiber matrix is composed of a metal or metalloid oxide. After reaction of the solid phase extraction material with a silane, the silane is covalently attached to the inorganic substrate via an oxygen linkage, and the metal or metalloid oxides are functionalized by, for example, hydrocarbyl, amido, carbamyl, carbamato, urethane, carbamido, isocyanato, diol, glycidoxy, ethoxy, propoxy, carbonyl, carboxy, acetonyl, thio, dithio, hydroxy, ether, sulfinyl, sulfonyl, sulfonic acid, sulfate, sulfonamido, amino, nitrilo, isonitrilo, epoxy, guanidino, nitro, nitroso, and phosphate. In a preferred embodiment, the functionalized monolithic sorbent contains bonded silica. The silica can be chemically treated (or functionalized) by any method known in the art. In a preferred embodiment, the silica is bonded with alkyl moieties, typically $C_{2-30}$ alkyl groups, to render the silica hydrophobic.

Methods are also provided for preparing a device for solid phase extraction. The following steps are generally used: inserting a functionalized monolithic sorbent into a hollow tube having one broader opening and one narrower opening; applying reduced pressure to the narrower opening of the tube to insert the functionalized monolithic sorbent into the tube; applying positive pressure to the broader opening of the tube to insert the functionalized monolithic sorbent into the narrow opening of the tube; and compacting the functionalized monolithic sorbent.

In a preferred embodiment, the solid phase extraction device is a solid phase extraction pipette, and the hollow tube having one broader opening and one narrower opening is a pipette tip. Generally, the functionalized monolithic sorbent is placed in the smaller opening of the pipette by the following steps: inserting the functionalized monolithic sorbent into the larger opening of the pipette; applying reduced pressure to the smaller opening of the pipette to insert the functionalized monolithic sorbent; applying positive pressure to the larger opening of the pipette to insert the functionalized monolithic sorbent into the pipette tip; and compacting the functionalized monolithic sorbent. Typically, the reduced pressure is about 25 inches of mercury, and the positive pressure is from about 95 psi to about 110 psi and more typically about 100 psi.

Methods are also provided for preparing a sample for analysis, generally including the steps of: activating a solid phase extraction pipette; adsorbing components of a sample to be analyzed onto the solid phase extraction pipette; washing the solid phase extraction pipette with a solvent which does not remove adsorbed analytes from the solid phase extraction material; washing the solid phase extraction pipette with a solvent that does remove adsorbed analytes from the solid phase extraction material; and collecting the analytes.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Figure 1:
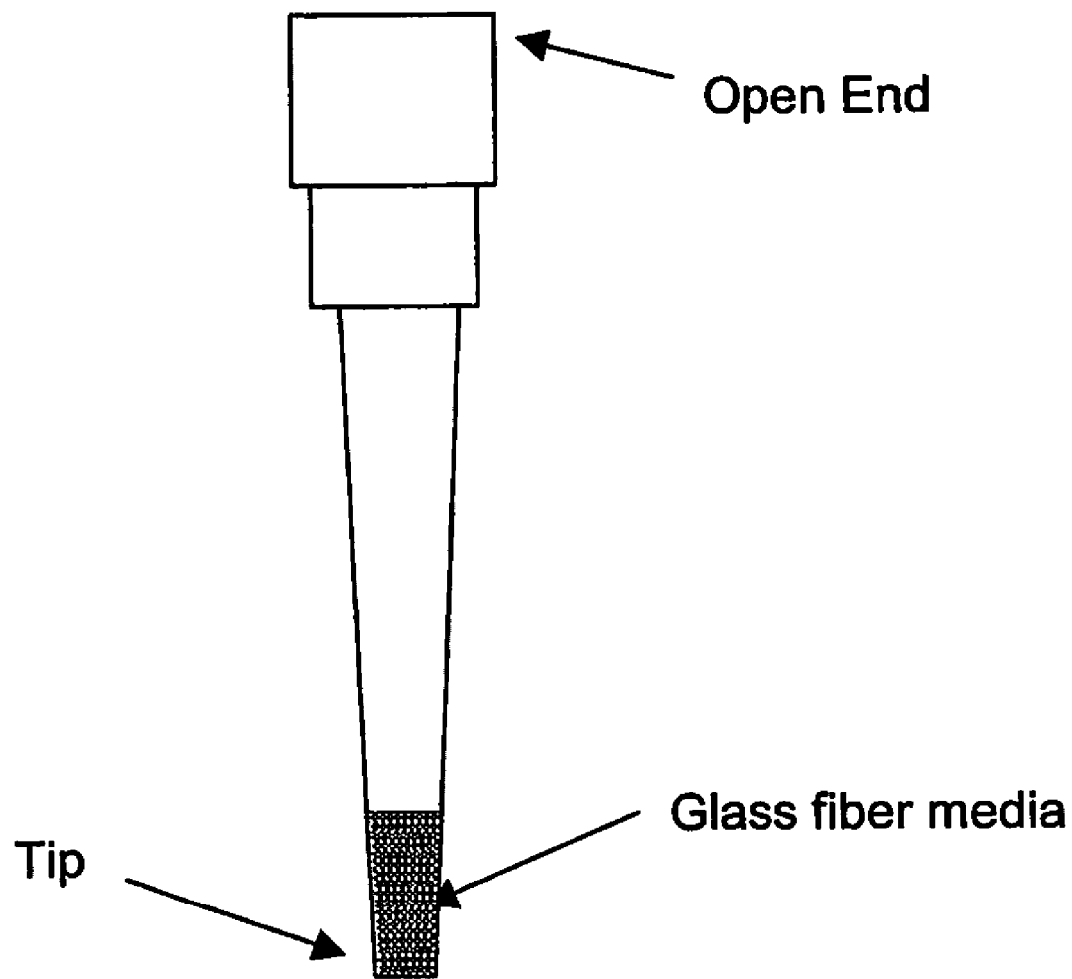
FIG. 1 illustrates one embodiment of a solid phase extraction device.

Before the present invention is described in detail, it is to be understood that unless otherwise indicated this invention is not limited to specific pipette tips shapes, sizes, or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a solvent" includes two or more solvents; reference to "an analyte" includes two or more analytes, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "pipette" refers to the fluid contacting portion of a pipette, generally a disposable pipette tip that is used in conjunction with a pipetter used for dispensing small quantities of fluids.

As used herein, the term "slug" is used to indicate a mass of the solid phase extraction material.

As used herein, the term "functionalized monolithic sorbent" refers to a glass fiber matrix containing bonded phase metal oxides, preferably silica.

Glass fiber filters are known in the art as being useful in connection with filtration, however, this material is believed to possess too little surface area to be suitable for solid phase extraction, and in fact, glass fibers have generally been viewed as inert and nonadsorptive to chromatographic or analytical procedures. Thus, glass fibers have been utilized in SPE primarily as retention means for the sorbent, and not as SPE adsorptive material in itself, notwithstanding reports that the filter itself may result in loss of sample as suggested in U.S. Pat. No. 6,416,716. The present inventors have made the surprising discovery that glass fiber matrices embedded with bonded phase silica can be formed into a functionalized monolithic sorbent in a solid phase extraction pipette having a high adsorptive capacity for analytes, while retaining good flow properties and reproducibility in performance and manufacturing. Conventional means of manipulating the glass fiber matrices embedded with bonded phase silica to form solid phase extraction devices for extraction of micromolar and smaller amounts of analytes proved impractical due to damage to the delicate glass fiber matrix. However, the present inventor has made the surprising discovery that a solid phase extraction pipette containing a functionalized monolithic sorbent comprised of glass fiber matrices containing bonded phase silica can be formed using a combination of reduced pressure, positive pressure and mechanical compaction that results in the highly reproducible preparation of solid phase extraction sorbent inside a pipette tip having good flow properties and both excellent retention and recovery of analytes.

Accordingly, solid phase extraction devices are provided for sample preparation, comprising a hollow conical tube having one narrower opening and one broader opening, wherein the narrower opening of the tube contains a solid phase extraction material comprising a functionalized monolithic sorbent, wherein the solid phase extraction device is prepared by a combination of reduced pressure, positive pressure and mechanical compaction. In a preferred embodiment, the solid phase extraction device is a pipette having a smaller opening and larger opening and a functionalized monolithic sorbent placed in the smaller opening (or tip) of the pipette. The functionalized monolithic sorbent is placed in the smaller opening of the pipette by a combination of reduced pressure, positive pressure and mechanical compaction.

These devices and methods for preparing and using the devices are described in greater detail below.

II. Solid Phase Extraction Devices

A. Device Specifications

The solid phase extraction device comprises a hollow conical tube, which can take a variety of forms, shapes and dimensions. Typically, the tube will have a circular cross-section, but in principle, the tube can be oval, square, rectangular, or irregular, and the like, so long as the solid phase material can be placed into the tube to provide high flow characteristics. The hollow tube can be constructed of any material suitable for holding and dispensing liquids, and will generally be a polymeric material such as a polyolefin, fluorinated polymers, polysulfone, polyethersulfone, cellulose acetate, polystyrene, polystyrene/acrylonitrile copolymer, PVDF, and the like. Polyolefinic materials are preferred, for example, polypropylene, polyethylene, poly(tetrafluoroethylene), or copolymers thereof. For nonaqueous liquids, the tube can be constructed of a material that will not dissolve or leach contaminants into the nonaqueous liquid. Preferably, the devices are constructed from ultra-clean polymers, preferably polypropylene.

Figure 2:
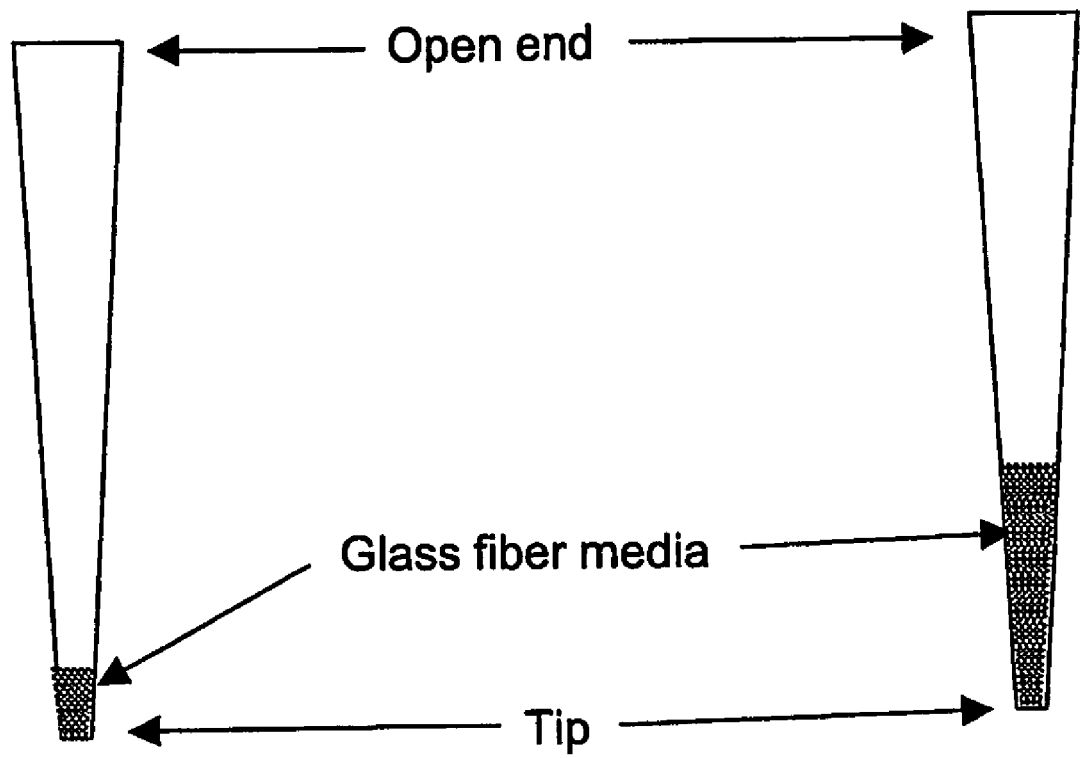
FIG. 2 illustrates additional embodiments of a solid phase extraction pipette utilizing varying amounts of sorbent.

In a preferred embodiment, the solid phase extraction device is in the form of a pipette tip that can be used with any conventional manual or automated pipetting device. The pipette tip is not limited to any particular size or shape or construction material. The functionalized monolithic sorbent can occupy a variable amount of the volume of the pipette tip, for example, at least up to about 10% of the usable volume of the pipette tip. Representative embodiments are shown in FIGS. 1 and 2.

B. Solid Phase Extraction Materials

The solid phase extraction material is a functionalized monolithic sorbent, comprising a glass fiber matrix embedded with a bonded phase comprising a metal oxide or metalloid oxide having reactive metal oxides capable of reacting with silanes, such as alkoxysilanes, aminosilanes, hydroxysilanes or halosilanes. Suitable metal oxides and metalloid oxides include silica, alumina, zeolite, mullite, zirconia, vanadia or titania, or mixtures or composites thereof. Likewise, the glass fiber matrix is composed of a metal or metalloid oxide. After reaction of the solid phase extraction material with a silane, the silane is covalently attached to the inorganic substrate via an oxygen linkage, and the metal or metalloid oxides are functionalized by, for example, hydrocarbyl, amido, carbamyl, carbamato, urethane, carbamido, isocyanato, diol, glycidoxy, ethoxy, propoxy, carbonyl, carboxy, acetonyl, thio, dithio, hydroxy, ether, sulfinyl, sulfonyl, sulfonic acid, sulfate, sulfonamido, amino, nitrilo, isonitrilo, epoxy, guanidino, nitro, nitroso, and phosphate.

In a preferred embodiment, the functionalized monolithic sorbent contains bonded silica. The silica can be chemically treated (or functionalized) by any method known in the art. In a preferred embodiment, the silica is bonded with alkyl moieties, typically $C_{2-30}$ alkyl groups, to render the silica hydrophobic. Any bonded phase that can be used to modify silica is possible, such as amino, cyano, glycidyl, and the like, as well as anion or cation exchange groups, as discussed above.

In a particular embodiment, the functionalized monolithic sorbent is comprised of glass microfibers impregnated with modified silica, preferably prepared using organosilane chemistries, available from Varian, Inc., Lake Forest, Calif., which are similar to the SPEC® product. This monolithic bonded silica allows greatly improved flow. The monolithic design throughout the membrane results in highly efficient mass transfer compared with packed-bed SPE columns. With the monolithic design, there is much less void volume and less solvent is used in sample processing. The binding capacity of the functionalized monolithic sorbent is generally in the range of about 1 microgram analyte per 0.1 mg sorbent.

The glass fiber matrix forms a porous labyrinth allowing high flow characteristics while ensuring high retention of analytes. The glass fiber matrix material typically is constructed from randomly distributed fibers which create a tortuous path of nominally rated size. In certain embodiments, the glass fiber matrix has a thickness of from about 0.1 to about 2 millimeters (mm), and typically has a thickness of about 1 mm.

The flow properties of the solid phase extraction pipette can be conveniently assessed by determining the flow of atmosphere through the pipette tip from the larger opening to the tip, when the tip of the pipette is connected to a vacuum source. Solid phase extraction pipettes prepared by the methods described herein develop a vacuum across the functionalized monolithic sorbent at a rate of about 1 inch of mercury in about 2-3 seconds when the pipette tip is connected to a vacuum source while measuring the development of a vacuum on the end having a larger opening. These flow rates provide good performance even for viscous sample solutions.

It is important that the method of preparing the solid phase extraction pipettes provide reproducible results, as precious samples can be lost by using pipette tips that do not exhibit adequate flow characteristics. Using the methods described herein, solid phase extraction pipettes are providing having uniform flow through the monolithic sorbent, which also results in greater reproducibility and superior performance.

III. Methods for Preparing Solid Phase Extraction Devices

Methods are also provided for preparing a device for solid phase extraction. The following steps are generally used: inserting a functionalized monolithic sorbent into a hollow tube having one broader opening and one narrower opening; applying reduced pressure to the narrower opening of the tube to insert the functionalized monolithic sorbent into the tube; applying positive pressure to the broader opening of the tube to insert the functionalized monolithic sorbent into the narrow opening of the tube; and compacting the functionalized monolithic sorbent.

In a preferred embodiment, the solid phase extraction device is a solid phase extraction pipette, and the hollow tube having one broader opening and one narrower opening is a pipette tip. Generally, the functionalized monolithic sorbent is placed in the smaller opening of the pipette by the following steps: inserting the functionalized monolithic sorbent into the larger opening of the pipette; applying reduced pressure to the smaller opening of the pipette to insert the functionalized monolithic sorbent; applying positive pressure to the larger opening of the pipette to insert the functionalized monolithic sorbent into the pipette tip; and compacting the functionalized monolithic sorbent. Typically, the reduced pressure is about 25 inches of mercury (625 torr or 12 psi), and the positive pressure is from about 95 psi (4,913 torr) to about 110 psi (5,689 torr) and more typically about 100 psi (5,171 torr).

A generalized procedure for preparing solid phase extraction pipette tips is described as follows. A chemically treated glass fiber filter material is used as the solid phase extraction matrix. A preferred glass fiber filter material is an alkyl functionalized monolithic sorbent manufactured by Varian, Inc., Lake Forest, Calif. (similar to the material sold under the tradename SPEC®-C18) a glass fiber material containing bonded phase silica. The glass fiber filter is cut into slugs of appropriate size, depending on the size of the pipette tip or other device and the quantity of solid phase extraction material desired. The quantity of solid phase material generally is chosen to occupy at least about 10% of the useable volume of the pipette tip, although the quantity is not critical and larger or smaller amounts can be used if desired. Typically for a 10 µL pipette tip, the glass fiber material is cut into the narrow strips (e.g., about 2-7 mm), and each strip is then cut again into smaller portions (e.g., 0.43-0.50 mm or as desired) for insertion into a pipette tip. The glass fiber material can be cut by any method desired, for example, by hand or using a mechanical cutter (e.g., Biodot, Inc. Irvine, Calif.). A single pipette tip is loaded with a single slug of solid phase extraction media. The glass fiber matrix is initially inserted by applying vacuum (e.g., using a vacuum pump) in the range of approximately 25 inches of mercury to one end of the tip. Then the glass fiber matrix is further packed in by the use of dry high-pressure air (e.g., using an air compressor). The high pressure air is generally in the range of approximately 95 to 110 psi, typically 100 psi. Finally, the media can be set in place by compacting the back end of the media slug using a stainless steel needle having a diameter matching the inner diameter of the pipette tip at the top of the glass fiber bed. Using a needle having a diameter matching the inner diameter of the pipette provides a gentle non-destructive compaction and further secures the glass fiber matrix in place inside the pipette tip. The choice of needle size can also be selected to control the amount of compaction force applied.

Figure 3:
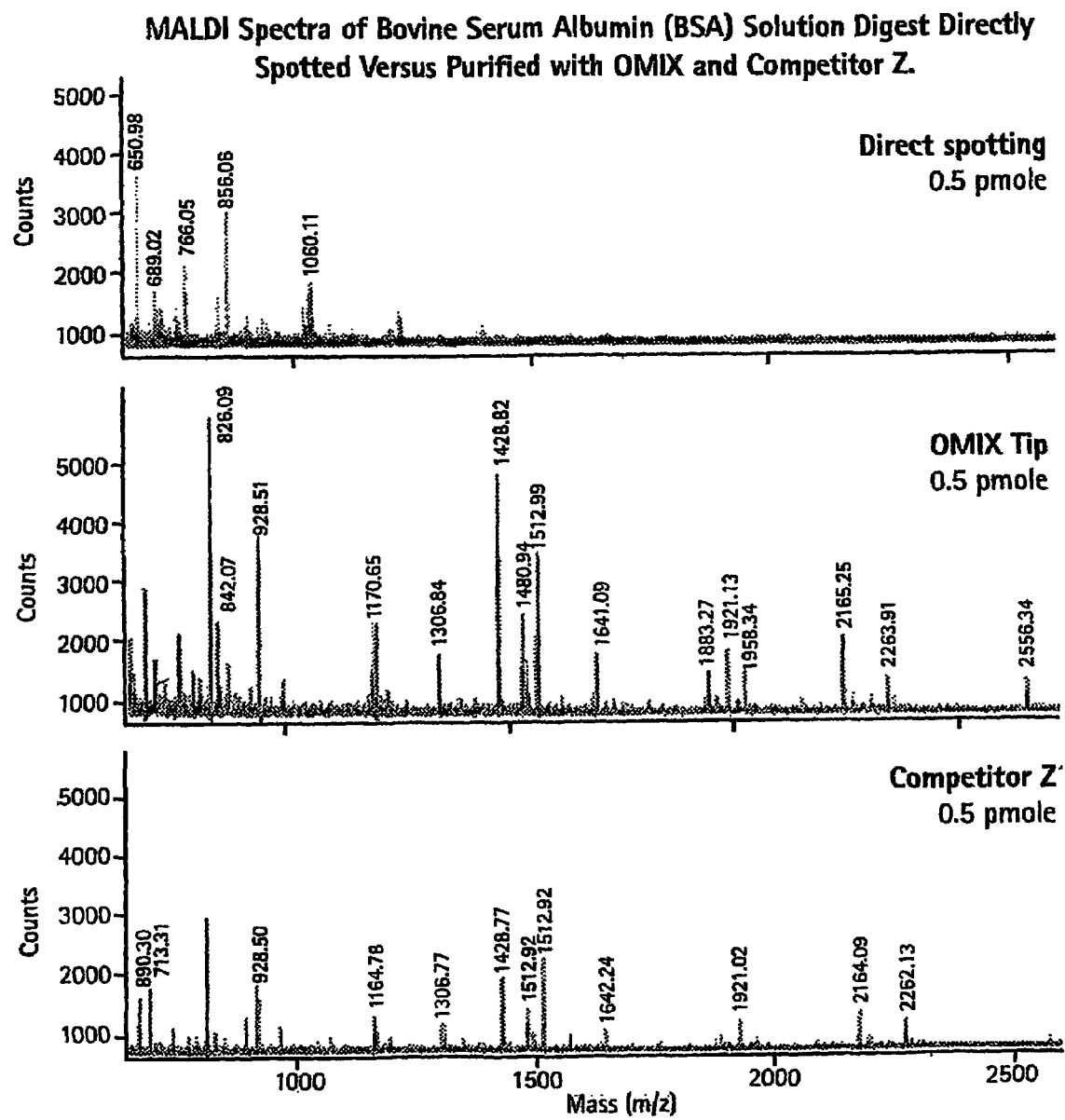
FIG. 3 illustrates the recovery of peptides from a sample under conditions of no treatment, treatment using a solid phase extraction pipette prepared as described herein and a solid phase extraction pipette prepared by an alternative manufacturer.
Figure 4:
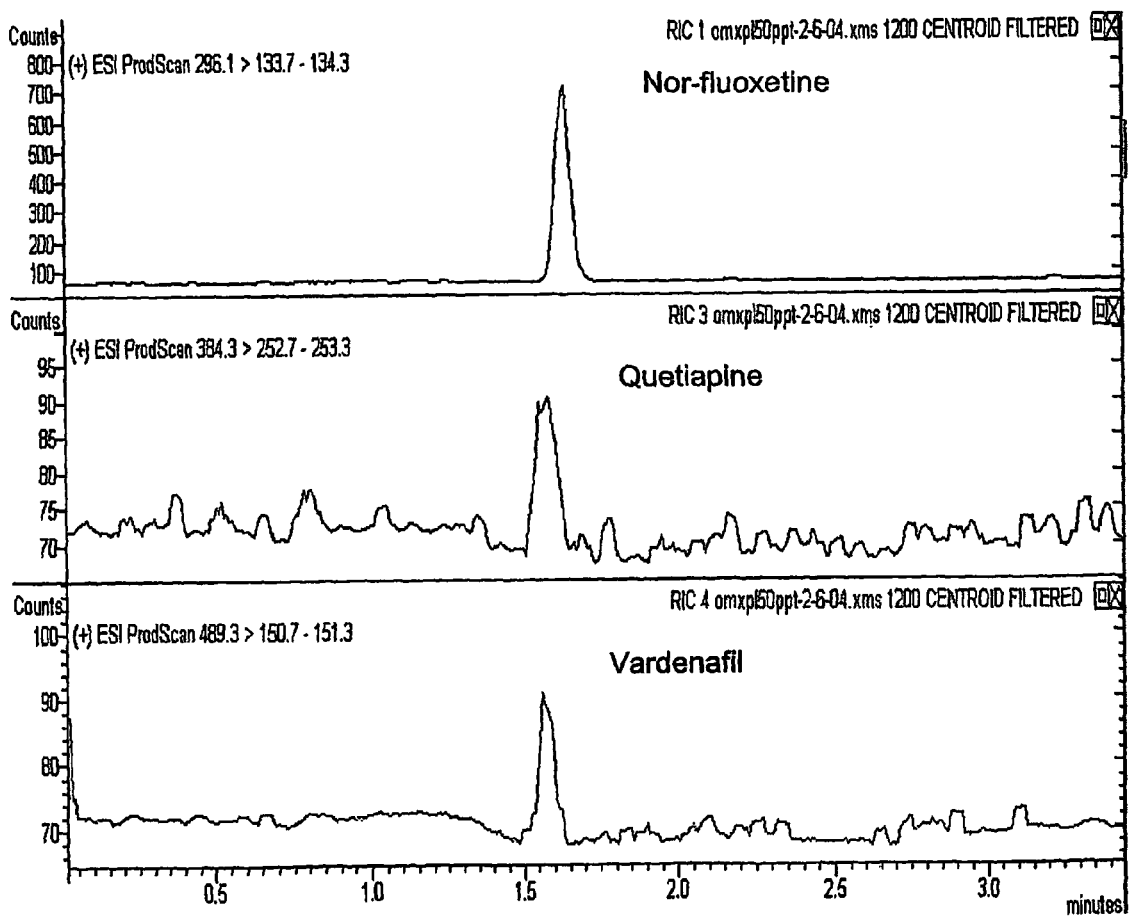
FIG. 4 illustrates a HPLC chromatogram showing the presence of drugs from plasma recovered using a solid phase extraction pipette prepared as described herein.

The solid phase extraction pipette tip prepared using the above method possesses a reversed phase adsorption capability, useful for adsorbing drugs or other hydrophobic compounds from aqueous samples. The pipette tips were tested as described in Examples 3 and 4 below and provided excellent recovery of compounds from solution and clean analytical results as demonstrated by both HPLC and MALDI-TOF. These results are demonstrated in FIGS. 3 and 4.

Of course, one skilled in the art will recognize that these methods can be applied to glass fiber matrices containing any bonded silica known in the art or discovered in the future. Some nonlimiting examples of bonded phases that can be prepared include those containing the following functionalizing agents: hydrocarbyl (e.g., $C_{2-30}$ alkyl, alkenyl, alkynyl), —NHC(O)— (amido), —C(O)NH— (carbamyl), —OC(O)NH— (carbamato), —NHC(O)O— (urethane), —NHC(O)NH— (carbamido or urea), —NCO (isocyanato), —CHOHCHOH— (diol), $CH_2OCHCH_2O$— (glycidoxy), —$(CH_2CH_2O)_n$— (ethoxy), —$(CH_2CH_2CH_2O)_n$— (propoxy), —C(O)— (carbonyl), —C(O)O— (carboxy), $CH_3C(O)CH_2$— (acetonyl), —S— (thio), —SS— (dithio), —CHOH— (hydroxy), —O— (ether), —SO— (sulfinyl), —$SO_2$— (sulfonyl), —$SO_3$— (sulfonic acid), —$OSO_3$— (sulfate), —$SO_2NH$—, —$SO_2NMe$— (sulfonamido), —NH—, —NMe—, —$NMe_2^+$—, —$N[(CH_2)_n]_2^+$— (amino), —CN (nitrilo), —NC (isonitrilo), —CHOCH— (epoxy), —NHC(NH)NH— (guanidino), —$NO_2$ (nitro), —NO (nitroso), and —$OPO_3$— (phosphate), where Me refers to methylene or methyl, and where n is an integer up to 30, generally less than 10. Many other examples are also known and are readily adapted to the devices and methods disclosed herein.

Using these general procedures, devices of other configurations can be made. SPE devices utilizing pipette tips are a preferred embodiment, but one skilled in the art will readily envision additional applications and sizes and configurations of devices that are adaptable to the methods described herein. Pipette tips of varying sizes and shapes can be prepared, as well as columns, capillaries, and tubes can be prepared using these methods. The methods are particularly well suited for preparing SPE devices using tubes and capillaries having tapering dimensions, such as conical shapes, which present a challenge to inserting delicate sorbent materials into the small spaces necessary to prepare microextraction devices.

IV. Methods for using Solid Phase Extraction Devices in the Preparation of Samples for Analysis.

The solid phase extraction devices can be used in a variety of ways to prepare samples for further analysis. In one embodiment, the solid phase extraction device can be used to remove undesired components from a mixture of analytes, such as contaminants, salts or other compounds present in a sample to be analyzed. The solid phase extraction material retains analytes having desired adsorptive characteristics, while undesired components are not adsorbed, and are dispensed out of the pipette tip and can be stored, further analyzed or discarded, as desired.

In another embodiment, the solid phase extraction device can be used to adsorb and enrich a particular component from a sample solution, while not adsorbing other components having different chemical characteristics. For example, an alkyl bonded phase monolithic sorbent can be used to selectively adsorb hydrophobic compounds from a sample, while more polar compounds are not adsorbed. Polar compounds can be selectively adsorbed using a bonded phase containing anion or cation exchange moieties, while the more hydrophobic compounds in a sample are not adsorbed. Combinations of the two are likewise possible, allowing adsorption of all compounds of interest from a sample, and eluting using the different eluants, either to elute the compounds adsorbed via a hydrophobic mechanism or the compounds adsorbed via ion exchange mechanism.

Methods for preparing a sample for analysis, generally include the steps of: activating a solid phase extraction pipette; adsorbing components of a sample to be analyzed onto the solid phase extraction pipette; washing the solid phase extraction pipette with a solvent which does not remove adsorbed (or retained) analytes from the solid phase extraction material; washing the solid phase extraction pipette with a solvent that does remove adsorbed (or retained) analytes from the solid phase extraction material; and collecting the analytes. A typical method of using a SPE device includes (1) activating or conditioning the SPE device with an organic solvent such as methanol or acetonitrile, or mixtures of organic solvents with water, optionally containing buffers or ion pairing reagents such as trifluoroacetic acid or formic acid; (2) equilibrating the SPE device with an aqueous solution, again optionally containing buffers or ion pairing reagents; (3) adding a sample containing analytes (which may or may not contain interfering components) to the SPE device; (4) washing the SPE device with an aqueous solution to remove undesired or nonadsorbed components; and (5) eluting the adsorbed analytes with a suitable eluting solvent, typically a mixture of organic and aqueous solvents. In some cases, for example, for a monolithic sorbent functionalized to possess ion exchange capabilities, the initial activation step may be optional. Typical protocols are described in the Examples.

The SPE devices described herein are adapted to be used for preparation of small sample volumes for analysis. However, the starting volume is not particularly limited to small volumes, and a relatively large amount of solvent can be adsorbed onto the functionalized monolithic sorbent, and then eluted in a much smaller volume, as desired. Typically, the device is adapted for the preparation of small volumes of sample, such as sample volumes ranging from about several microliters or below to about 1 ml, but in principle, it can be used with sample volumes up to about $10^3$ ml.

It is to be understood that while the invention has been described in conjunction with the preferred specific embodiments thereof, that the description above as well as the examples that follow are intended to illustrate and not limit the scope of the invention. The practice of the present invention will employ, unless otherwise indicated, conventional techniques of organic chemistry, polymer chemistry, biochemistry and the like, which are within the skill of the art. Other aspects, advantages and modifications within the scope of the invention will be apparent to those skilled in the art to which the invention pertains. Such techniques are explained fully in the literature.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric. All solvents were purchased as HPLC grade.

Abbreviations:
SPEC®-C18 bonded phase silica functionalized using an alkyl chain of 18 carbons in length (from Varian, Inc., Lake Forest, Calif.)
MALDI-TOF matrix-assisted laser desorption ionization-time of flight mass spectrometry
HPLC high performance liquid chromatography
TFA trifluoroacetic acid

EXAMPLE 1

A general procedure for preparing solid phase extraction pipette tips is described. A chemically treated (C-18 modified silica) sheet of glass fiber filter material (Varian, Inc., Lake Forest, Calif.) was cut into narrow strips (about 2-7 mm). Each strip was then cut again into media slugs (0.43-0.50 mm) for insertion into a pipette tip. A single pipette tip was loaded with a single slug of solid phase extraction media. The media was initially inserted by applying vacuum (approximately 25 inches of mercury) to one end of the tip as it was cut. Then the media was further packed in by the use of high-pressure air under dry conditions using an air compressor (approximately 100 psi). Finally, the media was set in place by gently compacting the back end of the media slug using a stainless steel needle having a diameter matching the inner diameter of the pipette tip at the top of the glass fiber bed.

The solid phase extraction pipette tip prepared using the above method possessed a reversed phase adsorption capability, useful for adsorbing drugs or other hydrophobic compounds from aqueous samples. The pipette tips were tested as described in Examples 3 and 4 below.

EXAMPLE 2

The procedure of Example 1 is followed, using glass fiber filter material chemically modified to possess amine moieties (Varian, Inc., Lake Forest, Calif.) to prepare a solid phase extraction pipette having a modified adsorption capability.

EXAMPLE 3

A solid phase extraction pipette tip prepared using the method described in Example 1 was used to prepare a mixture of peptides produced by the proteolytic digestion of bovine serum albumin for mass spectrometric analysis.

The solid phase extraction pipette tip was assembled onto the pipetter and activated by pipetting 10 µL of 50% acetonitrile twice followed by pipetting 10 µL 0.1% trifluoroacetic acid (TFA) twice. In a test tube, 5 µL of the mixture of peptides (0.5 pmoles) and 5 µL 1% TFA were added and vortexed briefly. The pretreated sample containing the mixture of peptides was loaded onto the solid phase extraction pipette by pipetting 10 µL of the sample and slowly expelling the sample out of the pipette tip. The pipette tip was washed by pipetting 10 µL of 0.1% TFA and expelling the solution. Finally, the adsorbed compounds were eluted by pipetting 2 µL 50% acetonitrile/0.1% TFA, which was analyzed without further treatment by MALDI-TOF.

For comparison, an untreated sample of peptides (0.5 pmoles) and a sample of peptides (0.5 pmoles) prepared using a pipette tip produced by competitor Z were also analyzed by MALDI-TOF. The results, shown in FIG. 3, demonstrate the interference caused by ion suppression in untreated samples, and the excellent recovery of peptides when using the solid phase extraction pipette tip prepared according to the method described in Example 1. The recovery of peptides was at least two to three times greater when using the solid phase extraction pipette prepared by the method described in Example 1 in comparison to the pipette tip prepared by competitor Z. Even greater recoveries were seen in comparison to untreated sample.

EXAMPLE 4

A method was developed for analyzing plasma concentrations of vardenafil and quetiapine using a bovine model. In brief, blank bovine plasma was spiked with the appropriate amounts of vardenafil and quetiapine solutions. Standard curves were generated using known concentrations of vardenafil and quetiapine as follows: 1.0 and 10.0 ng/mL standard solutions were prepared in 50:50 MeOH: 10 mM Aq. HCOOH. Appropriate amounts were diluted into test tubes to prepare known concentrations of each drug. Aliquots were removed for analysis having a known amount of each drug and the signal detected was used to prepare a standard curve.

In a test tube, 50 μL bovine plasma and 10 μL internal standard (100 ng/mL norfluoxetine in 25% aqueous methanol) were added and vortexed briefly. Forty μL ammonium acetate (pH~9) was added and vortexed briefly. A solid phase extraction pipette tip containing a C-18 reversed phase extraction phase was prepared by pipetting 100 μL of 100% methanol twice followed by pipetting 100 μL 5 mM ammonium acetate (pH~9) twice. The sample was loaded onto the solid phase extraction pipette by pipetting 100 μL pre-treated sample and slowly expelling the sample out of the pipette tip. The pipette tip was washed by pipetting 100 μL of 5% aqueous methanol and expelling the solution. The solid phase was dried by quickly pipetting air through the tip 2-4 times. Finally, the adsorbed compounds were eluted by pipetting 25 μL 95:5 MeOH: 10 mM aqueous HCOOH twice to generate 50 μL total elution volume, which was analyzed directly by HPLC. The results are demonstrated in FIG. 4.

EXAMPLE 5

A comparison of solid phase extraction pipettes prepared using the methods described herein with pipettes prepared by competitor Z was performed. Pipette tips were sampled at random from 3 racks containing pipette tips from a competitor and pipette tips prepared by the methods described herein, and tested for ability to extract analytes. Nineteen failures (0% recovery) were detected in the pipette tips prepared by competitor Z (18% failures among tips tested), while none were detected among pipette tips prepared by the presently described methods (0% failures among tips tested).

In addition, the percent recovery and relative standard deviation of recovery of analytes for pipette tips prepared by the methods described herein were compared with pipette tips prepared by competitor Z. The percent recovery and relative standard deviation for three different peptides, TFQAYPL-REA (SEQ ID NO:1), RTKRSGSVYEPLKI (SEQ ID NO:2), and LWMRF (SEQ ID NO:3) was measured for the two different pipette tips. Use of pipette tips prepared by the methods described herein resulted in up to 38% improved recoveries and up to 3-fold improved relative standard deviations (improved precision) in comparison with pipette tips prepared by competitor Z.

This comparison illustrates the superior reproducibility of the method of preparing the solid phase extraction pipettes as well as the superior flow and adsorption properties provided by the superior solid phase extraction material utilized.

What is claimed is:

1. A method for preparing a device for solid phase extraction, comprising the steps of sequentially:
    a) inserting a functionalized monolithic sorbent into a hollow tube having one broader opening and one narrower opening;
    b) applying reduced pressure to the narrower opening of the tube to insert the functionalized monolithic sorbent into the tube;
    c) applying positive pressure using a pressurized gas to the broader opening of the tube to insert the functionalized monolithic sorbent into the narrow opening of the tube; and
    d) mechanically compacting the functionalized monolithic sorbent;
    wherein said functionalized monolithic sorbent comprises a glass fiber matrix containing bonded phase metal or metalloid oxides.

2. The method of claim 1, wherein the solid phase extraction device is a solid phase extraction pipette.

3. The method of claim 1, wherein the reduced pressure is about 12 psi.

4. The method of claim 1, wherein the positive pressure is from about 95 psi to about 110 psi.

5. The method of claim 1, wherein the metal or metalloid oxide is silica, alumina, zeolite, mullite, zirconia, vanadia or titania, or mixtures, or composites thereof.

6. The method of claim 1, wherein the metal or metalloid oxide has reactive metal oxides capable of reacting with an alkoxysilane, aminosilane, hydroxysilane or halosilane.

7. The method of claim 1, wherein the monolithic sorbent is functionalized by hydrocarbyl, amido, carbamyl, carbamato, urethane, carbamido, isocyanato, diol, glycidoxy, ethoxy, propoxy, carbonyl, carboxy, acetonyl, thio, dithio, hydroxy, ether, sulfinyl, sulfonyl, sulfonic acid, sulfate, sulfonamido, amino, nitrilo, isonitrilo, epoxy, guanidino, nitro, nitroso, and phosphate.

* * * * *